US00PP09649P

United States Patent [19]

Williams

[11] Patent Number: Plant 9,649

[45] Date of Patent: Oct. 1, 1996

[54] SHRUB ROSE PLANT NAMED 'WILSCAR'

[76] Inventor: J. Benjamin Williams, 2800 Elnora St., Silver Spring, Md. 20902

[21] Appl. No.: 408,545

[22] Filed: Mar. 22, 1995

[51] Int. Cl.[6] ..... A01H 5/00

[52] U.S. Cl. ..... Plt./1

[58] Field of Search ..... Plt./1, 10, 7.1

[56] References Cited

U.S. PATENT DOCUMENTS

P.P. 7,116 1/1990 Meilland ..... Plt./1

*Primary Examiner*—Howard J. Locker

[57] ABSTRACT

A new and distinct variety of rose plant of the shrub rose class characterized by its dwarf and compact habit of growth.

1 Drawing Sheet

BACKGROUND OF THE NEW PLANT

The present invention relates to a new and distinct variety of rose plant of the shrub class named 'Wilscar', which was originated by my crossing as seed parent a 'Europeana' (U.S. Plant Pat. No. 2,540) F1 seedling with 'Red Fountain' (U.S. Plant Pat. No. 3,615) as the pollen parent.

Among the novel characteristics possessed by this new variety which distinguish it from its parents and all other varieites of which I am aware are its:

1. Attractive and unique color of bud (R.H.S. 45-A) and bloom (R.H.S. 45-B) with attractive bright yellow stamens and white eye, as compared to its parental cultivars which are both dark red;

2. Continuous blooming habit;

3. Disease resistance and winter-hardiness;

4. Low growing and vigorous spreading habit of growth, unlike the climbing habit of 'Red Fountain' and the upright growth of 'Europeana'; and 5. Semi-double bloom (eight petals) which is less than either parental cultivar.

Asexual reproduction by budding of the new variety as performed in McFarlin, Calif., and West Grove, Pa., shows the foregoing and other distinguishing characteristics come true to form and are established and transmitted through succeeding propagation.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Color Chart (R.H.S.C.C.). The terminology used in color description herein refers to plate numbers in the aforementioned color chart, e.g., "158-B" is plate 158-B of The Royal Horticultural Society Color Chart.

Description of the New Variety

Flower

A. Bud:
- (1) *Size.*—Small, 1 to 1.5 cm.
- (2) *Form.*—Pointed.
- (3) *Color.*—45-A.
- (4) *Sepals.*—Short, narrow and barely covering bud.
- (5) *Peduncle.*—Short and compact in cluster.

B. Bloom:
- (1) *Size.*—4–5 cm.

- (2) *Borne.*—Large sprays of 5 to 9 blooms per spray.
- (3) *Form.*—Flat and semi-double.
- (4) *Petalage.*—Number of petals under normal conditions is 8.
- (5) *Color.*—45-B.
- (6) *Color change.*—Color holds at 45-B throughout cycle.

C. Petals:
- (1) *Texture.*—Good substance, velvety on the inside surface and satiny on the outside surface.
- (2) *Appearance.*—Good substance and with a darker overlay on the inside surface.
- (3) *Form.*—Mostly flat.
- (4) *Arrangement.*—Semi-double with two rows of four petals.
- (5) *Petaloids in center.*—Few.
- (6) *Persistence.*—Drop off cleanly.
- (7) *Fragrance.*—Slight.
- (8) *Lasting quality.*—On the plant very long (12–15 days).

Reproductive Organs

A. Stamens:
- (1) *Anthers.*—Color 20-C.
- (2) *Pollen.*—Color 20-B.

B. Pistils:
- (1) Styles.—Even length.
- (2) Stigmas.—Color 145-C.

C. Hips: None observed.

Plant

A. Form: Dwarf and compact; 12 inches high, 4–6 feet spread after three years.

B. Growth: Low, prostrate.

C. Blooming habit: Continuous.

D. Foliage:
- (1) *Size.*—Small.
- (2) *Quantity.*—Abundant, commonly 3–5 leaflets per compounds leaf, 5–7 leaves develop on the main canes.
- (3) *Color.*—Juvenile foliage: Closest to 143-A. Mature foliage: Upper-side closest to 141-B. Under-side closest to 146-C.
- (4) *Shape.*—pointed.
- (5) *Texture.*—a) Upper side — semi-gloss. b) Under side — matte.
- (6) *Edge.*—Serrated.
- (7) *Leaf stem.*—Short, branched, color closest to 141-B.
- (8) *Stipules.*—Medium length; smooth.

E. Wood:

(1) *New wood.*—a) Color — medium green. b) Bark — smooth.

(2) *Old wood.*—a) Color — 147-B. b) Bark — smooth.

F. Thorns:

(1) *Quantity.*—Very few.

(2) *Form.*—Straight, slightly curved down.

(3) *Length.*—Short (0.5 cm).

(4) *Color.*—Light brown to russet brown.

(5) *Position.*—Irregular.

G. Prickles:

(1) *Quantity.*—Few.

H. Plant's disease resistance:

(1) *Mildew.*—Above average.

(2) *Blackspot.*—Above average.

(3) *Rust.*—Above average.

I. Winter hardiness.—Excellent.

I claim:

1. A new and distinct variety of rose plant of the shrub rose class, substantially as herein shown and described.

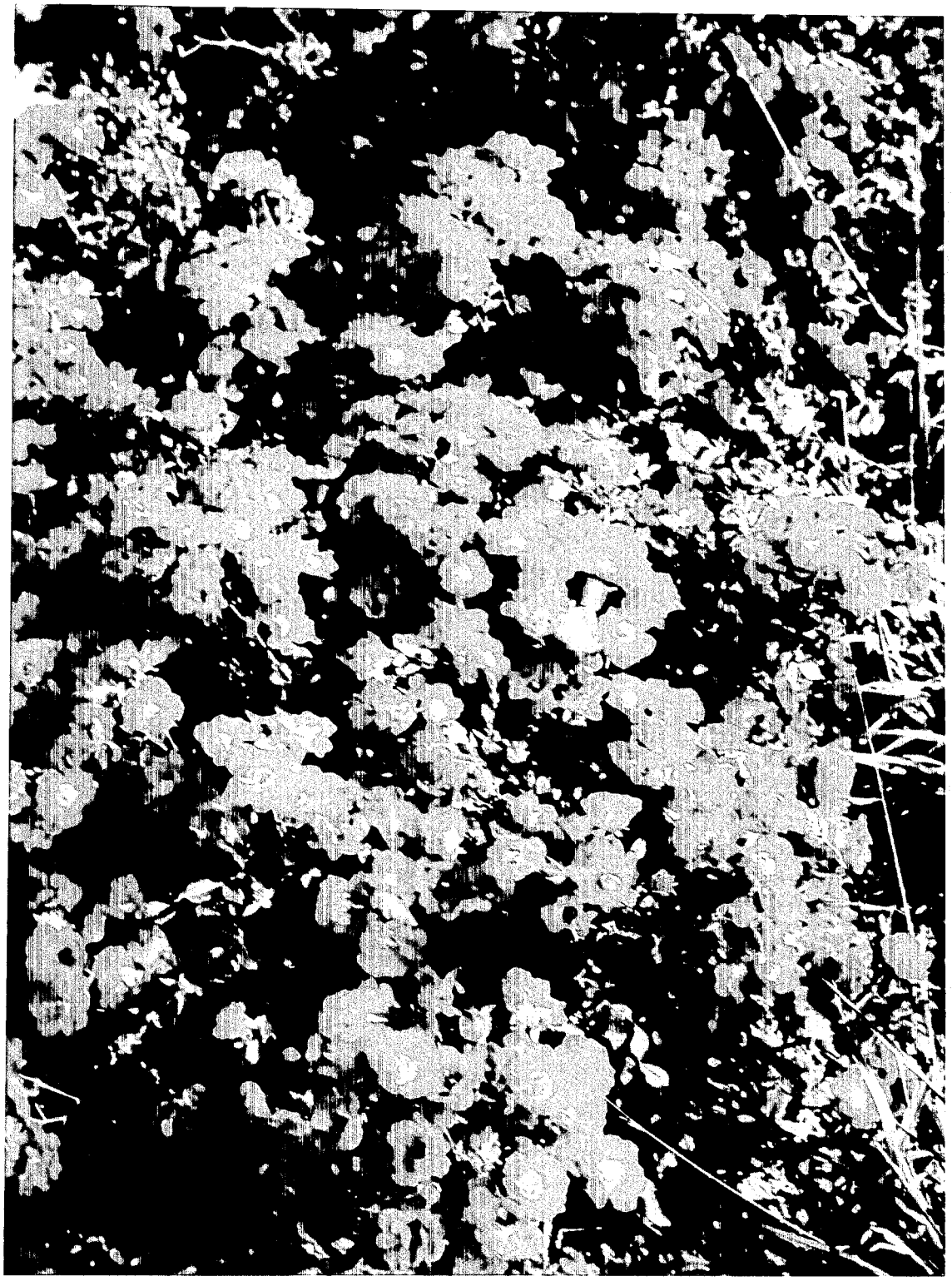

* * * * *